United States Patent [19]

Wikman-Coffelt

[11] Patent Number: 5,066,578

[45] Date of Patent: Nov. 19, 1991

[54] LONG-TERM PRESERVATION OF ORGANS FOR TRANSPLANTATION

[75] Inventor: Joan Wikman-Coffelt, Davis, Calif.

[73] Assignee: The Regents of the University of California, Oakland, Calif.

[21] Appl. No.: 455,562

[22] Filed: Dec. 21, 1989

[51] Int. Cl.$^5$ .............................................. A01N 1/02
[52] U.S. Cl. ...................................... 435/1; 435/240.2
[58] Field of Search ............................................. 435/1

[56] References Cited

U.S. PATENT DOCUMENTS 4,663,289  5/1987  Veech ................................. 435/240
4,959,319  9/1990  Skelnik .................................... 435/1

OTHER PUBLICATIONS

Kane–Chem. Abst. vol. 108 (1988) p. 34411y.
Edakuni–Chem. Abst., vol. 86 (1977), p. 53350w.
Cornell–Chem. Abst., vol. 100 (1984), p. 49243d.

*Primary Examiner*—Sam Rosen
*Attorney, Agent, or Firm*—Hana Dolezalova

[57] ABSTRACT

A novel method for preservation of organs for transplantation, wherein the organ to be transplanted is first perfused with a preservation solution containing essentially pyruvate, inorganic salts providing ions to retain the cell action potential and optionally a protein. Then, the organ is perfused with the second preservation solution containing the first solution and alcohol.

20 Claims, 5 Drawing Sheets

LONG-TERM PRESERVATION OF ORGANS FOR TRANSPLANTATION

BACKGROUND OF THE INVENTION

1. Field of the Invention

This invention concerns a novel and improved process, including novel preservation solutions, for long-term preservation of organs for transplantation. The preservation process comprises perfusing the organs such as liver, kidney, pancreas, spleen, brain, embryo, testicles, ovaries, lung or heart-lung complex, or washing organs such as cornea, skin or cartilage, with a first novel physiological preservation solution containing pyruvate, under normal physiological conditions and at a warm temperature to remove blood and other impurities and debris by the increased flow through the organ, bringing the organ to its basal metabolic rate stage with a second preservation solution containing pyruvate and a small percentage of alcohol and preserving the organ with diffusion of gases and nutrients from the media, by submerging and storing the organ in the first preservation solution at low but not freezing temperature for periods longer than 24 hours.

2. Related Disclosures

Organ transplantations, in particular transplantations of organs such as liver, kidney, lung, lung-heart complex, spleen, brain, testicles, embryo and skin, lens and cartilage have become an important tools in saving lives in patients with irreversibly diseased or damaged organs. With increasing incidence of the circulatory, cancerous, hereditary or infectious diseases in the population, the organ transplantation is used more and more to preserve a life of otherwise healthy individuals with badly damaged organs due to such diseases, infections, tumors and the hereditary or other conditions. Consequently, a demand for organs suitable for transplantation has risen substantially.

There are certain primary requirements for the organ to be suitable for transplantation. First, the organ must be healthy. Second, it must be transplanted or transplantable in certain time in which it is possible to preserve its normal physiological function. Third, it must be immunologically acceptable to the organ's recipient.

The first requirement can be only met by a physician removing the organ from the donor's body. The third requirement is increasingly being made possible by improved understanding of immune mechanism and method for preventing organ rejection by the recipient's immune system. The pharmaceutical industry is constantly developing and designing new immunosuppressant drugs which allow the easier immunological matching of the donor and the recipient and prevent, as much as possible, the organ rejection by recipient. Drugs such as azathioprine, monoclonal antibody muromonab-CD3, cyclophosphamide, cyclosporine and other recently discovered drugs such a for example drug known as FK-506 now allow the suppression of immune reactions for up to 6 months, at which time the body of the recipient is able to substantially rebuild proteins in the transplanted organ with their own proteins thus making it more immunologically acceptable. Moreover, when the graft tissue becomes accommodated within recipient's body, it can be maintained with relatively small and reasonably well tolerated doses of immunosuppressive drugs.

Consequently, the only remaining obstacle for the successful transplantation of organs is the preservation of their anatomical and functional integrity, in particular the preservation of their normal function for any length of time. With geographical spread of possible donors over the whole world, the length of time longer than 24 hours for preservation is extremely important.

There are several different circumstances involved in the organ transplantation. First, there is a group of organs which are metabolically highly active and have greater demands for supplies of oxygen and nutrients. In this group are organs such as heart, heart-lung complex, brain and embryo. The heart, brain and embryo in particular can be quickly and irreversibly damaged during extended time of ischemia caused by the insufficient supply of oxygen. These organs have to be prewashed by perfusion and brought to the basal metabolic state as soon as possible.

The second group of organs are the organs which have extensive vascularization and blood circulation and perform their function via such blood circulation by metabolizing, exchanging, releasing, detoxifying or eliminating certain compounds and gases in or out of the blood. These organs, while very active metabolically, are not as sensitive to the oxygen supply as is the first group of organs. Among these organs are liver, kidney, pancreas, spleen and lung. Since these organs contain large amounts of blood in their inner circulation, they also need to be prewashed by perfusion because the remnants of the blood and other tissue debris in their vessels may cause clotting of capillaries, and catabolic by-products such as iron, bile, aldehydes, etc., cause tissue acidity, alkalinity, or other homeostatic inequilibrium which may result in tissue damage.

The third and the least sensitive group of organs to the presence of oxygen and nutrients, used for transplantation are cartilage, cornea and skin. These organs do not have high requirement either for blood circulation or blood removal and the remnants of the blood and tissue debris may be simply washed in the oxygenated preservation solution. Their storage prior to transplantation could therefore continue for almost unlimited time if the suitable preservation solution containing oxygen and some energy supply is provided.

The ease of the organ preservation depends on their function which, in turn, determines their energy and oxygen demands.

The primary function of the heart is its continuous pumping of blood through the blood circulation system. That function depends on uninterrupted myocardial contractility which, in turn, depends on uninterrupted supply of energy and oxygen. Myocardial contractility must be preserved even during the time when the heart is removed from the donor and transplanted into the recipient. Since the contracting heart needs the constant supply of energy and oxygen, if these are not available, myocardial ischemia caused by inadequate circulation of blood to the myocardium develops which in turn results in irreversible destruction of the myocardial contractility.

The recently more often used heart-lung transplant is unique in that it requires a preservation of not only of myocardial function but also the alveoli-capillary exchange of gases. Consequently, it is important that even minuscule lung capillaries are preserved in the fully functional conditions. That requires a removal of all remnants of the blood and debris from the blood capillaries so that capillaries are not congested with the blood cells and debris, dead blood cells, blood clots or by blood catabolism by-products. The perfusion of heart-lung complex prior to preservation and storage is required.

The primary function of liver is metabolism, detoxification and the removal of the metabolic by-products and other toxic or potentially toxic materials from the blood, and redirecting these materials via blood connection to the kidney for the elimination from the body. The liver is one of the most vascularized organs in the body filled at any given time with a large amount of blood. Consequently, the liver also must be perfused before storing in the preservation solution and its metabolism must be decreased prior to transplantation.

Kidneys anatomical organization consists of extensive microcirculation interconnected with the complementary network of the excretory capillary system for elimination of catabolites, ions and water from the body. Prior to storing the kidney for transplantation, it is necessary to rinse away all blood from the renal vasculary bed. Spleen, which acts as a refuse for blood cells destruction by-products, is in the same group as kidney and liver and needs to be perfused before being transplanted. Testicles and ovaries are glandular organs which are reasonably vascularized and also would require perfusion to wash away the blood.

Because of their active function, liver, spleen and kidney have lively metabolism and may require energetic and nutritious supply. Consequently, in the interim between their removal from the donor's body and before transplanting them into a recipient's body, it is necessary to decrease their metabolism to a basal level.

Until now it has not been possible to successfully transplant the brain of one individual to another. Nevertheless, experimental designs exist and attempts are continuously made to bring such transplantation possibility about. Since the brain is the organ extremely sensitive to the deficiency of oxygen and energy supply, its preservation for transplantation, when feasible, will require a prior perfusion to remove all blood and other metabolites which could or would cross blood-brain barrier and also the use of the preservation solution with continuous perfusion which will allow the brain to exist in low metabolic state and provide at the same time essential nutrition, oxygen and energy to preserve sensitive nerve cells intact and fully functional.

Preservation of organs is currently commonly achieved by hypothermia and by perfusion with certain cardioplegic or other physiological solutions. The detailed description of the procedure for long-term preservation of the heart for transplantation is subject of concomitant and copending patent application entitled "Novel and Improved Technology for Preservation of the Heart for Transplantation", Ser. No. 07/455,580 filed Dec. 21, 1989, hereby incorporated by reference.

Surgical procedures including a removal of the organ for transplantation and inserting the organ to the donor body are individually specific to the organ but generally require a bloodless, relaxed and motionless field during operation. In the case of heart, this is currently accomplished by ischemic arrest induced by cross clamping the aorta which however causes myocardial ischemia. Any period of cardiac ischaemia and/or disrupted circulation to the organ resulting in organ ischemia is accompanied by metabolic and structural changes which determine the functional recovery of the organ in the postoperative period. The safe period of ischaemia for the human heart or for disruption of circulation in other organs and brain varies and is not clearly defined, but 20–30 minutes is generally considered to be the upper limit at least for heart, with much shorter periods for brain where even the short term oxygen deficiency may cause the irreversible damage to the nerve cells.

The need for protection of the organs during disruption of circulation has been well recognized and a number of methods including local and systemic hypothermia, intermittent perfusion, retrograde perfusion with cold blood, perfusion with cold lactated Ringer's solution, tetrodotoxin, acetylcholine, chemical asanguinous $K^+$ cardioplegia and cold blood cardioplegia and perfusion, have all been used in experimental studies and clinical practice in the field of organ transplantations. Of these, hypothermia and pharmacological treatments with various cold carioplegic or other solutions have now gained wide acceptance in clinical practice.

Hypothermia has been proved to be an effective method of organ preservation. It provides a decrease in organ metabolism, lowers the energy requirements, delays the depletion of high energy phosphate reserves and lactic acid accumulation, and retards the morphological and functional deterioration associated with disruption of blood supply. The technique of topical cooling with continuous irrigation of the surface of the organ was first described in *Surg. Gynaecol. Obst.,* 129:750 (1959). In this technique, the cooling proceeded from the surface of the organ to the interior but was unlikely to cool the internal organ tissue without profound hypothermia. Such moderate hypothermia and surface cooling have been generally found inadequate to protect the organ for more than one hour. Hypothermia with combined with improper solutions results in edema. Edema influences the voltage of the cells and destroys membrane potential integrity. On the other hand, deep hypothermia and surface cooling which is generally sufficient for 90 minutes from the organ removal is known to cause tissue damage due to crystallization of intracellular water and the membrane lipids. *Canad. Anaesth. Soc. J.,* 27:381 (1980). *Postgrad. Med. J.,* 59:11 (1983) reports that hypothermia slows all metabolic processes (thus conserving energy) including damaging degradative mechanisms and pathways which produce toxic metabolites. Hypothermia further leads to constriction and collapse of the vascular bed. The efficacy of hypothermia as a protective agent was reported as the post-ischemic recovery of function following a 60 minute period of ischemic arrest in the rat heart. In a case of the heart, reduction of the myocardial temperature from 37° C. to 4° C. during ischemia from resulted in a progressive improvement of post-ischemic recovery from 0% to 96% of preischemic function. The hypothermic protection is reported to be poor and falling off rapidly as the organ temperature rises above 28° C. In contrast, organ preservation below 24° C. temperature was reasonable for short time and was little improved with increasing degrees of hypothermia. The reason for the sharp inflection is unknown but might be related to lipoprotein phase transitions in cell membranes.

In view of the reported findings that (a) the moderate hypothermia is inadequate to protect the organ for more than one hour; (b) profound cooling of organ may cause cellular damage; and (c) that combination of appropriate protection solution with a mild hypothermia can only preserve the metabolically active organ functionally for about around 1–4 hours, it is clear that the technique which would be able to avoid deep hypothermia and still be able to preserve at least about 90% of normal function of organs after 24 hours post removal from the donor would be extremely advantageous.

The principles of successful preservation solution are a follows: energy conservation through the chemical induction of rapid and complete arrest of metabolic processes or at least slowing of metabolic rate to basal state and degradative processes through the coincident use of hypothermia and the prevention or reversal of certain unfavorable ischemia-induced changes with various protective agents.

Other attempts were made using various chemical means to achieve rapid offset of metabolic activity. Preservation solutions were investigated containing high concentrations of various ions such as potassium where infusion of a solution containing 16 mmol potassium chloride/litre caused decreased metabolism within a few seconds. The effect of this upon organ energy reserves and resistance to ischaemia has been investigated in a study in which isolated rat hearts were subjected to a 2 minute period of coronary infusion with a cardioplegic (16 mmol potassium/litre) or a non-cardioplegic (5 mmol potassium/litre) solution immediately following aortic cross clamping. After 30 minutes of ischaemia, the cardioplegic hearts contained 11.1 ±4.2 μmol of ATP/g dry weight and 9.4±2.1 μmol of creatinine phosphate/g dry weight, whereas the corresponding figures in the non-cardioplegic group were 5.3±0.9 and 2.8 ±0.4 μmol/g dry weight respectively. This striking difference in high energy phosphates was reflected in the post-ischemic recovery of function, which was zero in the non-cardioplegic group as opposed to almost 50% in the cardioplegic group.

Potassium is not unique in its ability to induce decrease in metabolism. Numerous other agents have been used clinically and/or experimentally, for example zero calcium, high magnesium, acetylcholine, neostigmine, tetrodotoxin and other pharmaceutical agents. In each instance, the primary protective effect has been through rapid induction of metabolic arrest and conservation of cellular energy supplies. KCl over longer period of time then 2 hours has led to vascular constriction. In the light of current knowledge, however, some agents such as zero calcium or tetrodotoxin could not be recommended for clinical use, or in case of transplantation of the heart or other organs, since they can cause cellular activity inequilibrium.

Successful preservation of the organ for transplantation depends on maintenance or restoration of its full physiological function.

The most commonly used preservation solutions for transplantation include crystalloid cardioplegia consisting of isotonic or slightly hypertonic saline supplemented with glucose and potassium chloride of which buffering capacity is usually afforded by the addition of sodium bicarbonate or THAM. In addition, some solutions contain small amounts of magnesium or calcium, glucose, ATP and creatine phosphate, while others contain pharmacologic agents such as mannitol, insulin, procaine or calcium channel blockers. Blood cardioplegia as a preservation medium was also investigated but was not better than the other cardioplegia.

Despite these advances in development of these preservation solutions, a significant percentage of patients continue to demonstrate clinical evidence of organ damage in the postoperative period (*New Engl. J. Med.*, 301:135 (1979), indicating that the current solutions for preservation of organs are not suitable for purposes of the organ preservation for transplantations for longer period of time.

For preservation of cellular mitochondrial function, it is important to arrest the organ metabolism immediately since significant utilization of high energy phosphates occurs during the brief period of organ's physiological activity between the onset of ischemia and the onset of a systole. *J. Thorac. Cardiovasc. Surg.*, 77:803 (1979); *J. Surg. Res.*, 24:201 (1978). This is particularly important since organ tissue recovery from prolonged global ischemia depends in part on the conservation of high energy phosphate stores and on the avoidance of reperfusion injury at the cellular level. *J. Mol. Cell. Cardiol.*, 13:941 (1981).

Decrease in cardiac performance due to insufficient supply of free energy is well documented. A reduction in contractile performance of isolated hamster heart correlates with a decrease in free energy of ATP hydrolysis. *Cardiac Adaptation to Hemodynamic Overload, Training and Stress.*, 197 (1983), Ed. R. Jacob et al., Steinkopff Verlag.

When the glucose was used as a sole substrate in isolated heart, the high energy phosphates ATP and phosphocreatine reached maximum values during heart diastole and minimum during systole. Upon exhaustion of ATP, a decrease in high level phosphate accompanied by a low level in the free energy of ATP hydrolysis, augmented levels of lactate and inorganic phosphate resulted in a 50% reduction of cardiac performance. *Cir. Res.*, 53:759 (1983). These results are equally applicable for other organ although probably depending on amount of mechanical or metabolic activity the organ is performing.

Since during the normal function of the organ the high level of energy is required, and since when the organ is removed from the donor for the transplantation the supply of oxygen and nutrients is limited to those amounts present in the organ prior to its removal or to those present in the preservation solution, and since the primarily used energy substrate glucose is metabolized in the muscle cells to lactate, the organ tissue soon faces a metabolic acidosis. Under any kind, but in particular under high work-load, conditions with glucose as a sole substrate, glycolytic production of pyruvate is inadequate to meet the energy needs under aerobic or anaerobic conditions, and consequently tissue, edema and acidosis develops. The acidosis, in turn may have a number of detrimental effects on organ function during disruption of circulation including cellular abnormalities and a reduction in functional performance, and gradual change in cellular homeostasis. Moreover, incomplete oxidation of glucose and the resultant increase in sugar phosphate is known to cause the cell edema which is very undesirable condition for the tissue preservation. Consequently, a suitable substitute for glucose would be advantageous.

Without the energy and nutrients supply, the metabolic depletion of intracellular ATP impairs the chance for post ischemic or post metabolic deficiency recovery of the organ performance. Thus, the same kind of energy providing substrate is necessary to be present in the preservation solution.

If glycolysis is rate limiting, there is reduced delivery of pyruvate to the intracellular mitochondria. By substituting pyruvate for loading the cells with glucose, glycolysis is bypassed and pyruvate is available to the mitochondria for oxidative phosphorylation producing free energy ATP. *Ann. J Physiol.*, 253: H 1261 (1987). Moreover, pyruvate does not cause cell edema. The use of pyruvate as a sole exogenous substrate results in greater functional and biochemical recovery.

Circ. Res., 35:448 (1974) reports that intracellular $Ca^{2+}$-overload leads to impaired oxidative phosphorylation, increased ATP breakdown and consequently inefficient ATP utilization for mechanical work.

Using the currently available organ preservation cardioplegic solutions, the safe time for organ survival is from 30 minutes to about 4 hours in human. As reported in Heart Disease, 1962 (1988), 3rd Ed., Harcourt Brace Jovanovich, within this period no significant tissue necrosis or permanent functional damage results. Under these conditions, Principles in Surgery, 407 (1984) 4th Ed., McGraw Hill, suggest that majority organs for transplantation in humans should be optimally implanted within 4 hours from the time of the organ removal.

Therefore, it would be advantageous for a worldwide transplantation network to extend this time period to possibly 24 hours or more. With the transportation feasibility to connect around the world in 24 hours, a supply of the various organs for transplantation could be widely improved and made practical if these organs were able to be fully functional after 24 hours.

It has been previously reported, that the metabolism of the organs is severely affected by ingestion of large amounts of alcohol. Changes such as impaired sodium, potassium stimulated ATPase activity, inhibition of sodium-calcium exchange, decreased fatty acid oxidation, depressed ATP, impairment of mitochondrial function and diminished ratios of phosphate to oxygen all lead to a reduction in organ function. While higher alcohol concentrations have been reported to produce a sudden cardiac arrest in the isolated hamster and rat heart, acute alcohol exposure reversibly depresses cardiac function without affecting energy resources. FASEB. J., 2:256 (1988) and Mag. Res. in Med., 8:58 (1988) reported that perfusion of the isolated hamster heart with 2% ethanol for 30 minutes showed decrease in developed pressure, a marked increase in enddiastolic pressure, a decrease in ATP and an increase in inorganic phosphate. There was no change in phosphocreatine or intracellular pH. After reequilibration, all the above values returned to almost normal levels showing that alcohol induced functional metabolic depression is reversible.

It is a primary object of this invention to provide an improved technology for long-time preservation of the organs for transplantation by using novel preservation solutions and process of using these solutions to achieve the almost complete functional restoration of isolated organs after 24 hours ischemia.

SUMMARY

One aspect of this invention is a novel and improved process for long-term preservation of organs for transplantation.

Other aspect of this invention is the preservation of the organ for period 24 hours or longer wherein at that time the organ recovers 90-100% of its original functional activity and around 70% of its intracellular mitochondrial metabolic activity.

Another aspect of this invention is preservation of the organs by sequence of events including a perfusion or washing of the organ, at a warm temperature, with the first preservation solution containing pyruvate for removal of the blood or other debris from organ's vessels, followed by the perfusion of the organ with the second preservation solution containing pyruvate and small percentage of ethanol in order to vasodilate the blood vessels, prevent edema, and achieve a rapid arrest of metabolic activity, to bring the metabolism to a basal rate stage, and to preserve the organ aseptically in the large volume of the first solution for 24 hours or longer at temperatures between 4°–10° C.

Still another aspect of this invention is the first novel preservation solution containing an optimal concentrations of ions, sodium chloride, potassium chloride, calcium chloride, sodium bicarbonate, sodium EDTA, magnesium chloride in admixture with sodium pyruvate and a protein.

Yet another aspect of this invention is the second preservation solution comprising the first preservation solution with additionally added ethanol.

Still another aspect of this invention is the prevention of development of metabolic acidosis and edema intracellularly by using the pyruvate to provide energy substrate but to eliminate cellular edema and the production of th acidic metabolite lactate formed during the previously used glucose as an energy supply.

Still yet another aspect of this invention is the decrease or arrest of metabolism achieved by the perfusion of organs with the second preservation solution, which results in a rapid and almost complete metabolic arrest due to the presence of alcohol in the second preservation solution and wherein such metabolic arrest is reversible after periods of storing in the first solution for as long as 24 hours with the recovery of the full functionality of the organ being at that time around 90% of the original activity.

DETAILED DESCRIPTION OF THE INVENTION

This invention concerns a novel and improved process for long-term preservation of the organs for transplantation. The preservation process comprises the following:

1. The organ is perfused at a warm temperature with a physiological preservation solution containing pyruvate to vasodilate, remove blood, increase flow, and load the cells with an energy supply in the form of a clean substrate, namely pyruvate. Pyruvate prevents edema, ischemia, calcium overload, and acidosis. It also helps preserve the action potential across the cell membrane.

2. Cannulation of the primary artery or vein incoming to the organ allows for a more complete exchange of gas, substrate, and media during perfusion and storage, thus allowing for usage of pyruvate as an energy source.

3. Perfusion with a second preservation solution containing both pyruvate and alcohol stops the organ from working (cross-bridge turnover), vasodilates vessels allowing for full vascular flow, continues to load the cells with pyruvate, and preserves the energy state of the organ.

4. Storage of the organ, via specific techniques, allows the organ to remain in a closed aseptic container for transfer, permitting diffusion of gases and media during the interim of 24 hour or longer transfer, retaining the organ in a healthy viable state. Unlike with other preservation solutions no edema, calcium loading, vasoconstriction or ischemia occurs.

A novel technology for long-term preservation of the organ for transfusion has been developed. The technology comprises of two novel preservation solutions and the sequential process of using these two solution to achieve the organ preservation for periods of 24 hours or longer after which time the organ recovers 90-100% of its normal functional activity and around 70% of its cellular mitochondrial metabolic activity. Until now no technology or preservation solution has been available to preserve organs for such long periods of time.

This technology is in particular useful for easy transportation of the organ without special requirements for unusual refrigerators or freezers and such transportation may be made in any type or kind of container which allows aseptic conditions, maintenance of temperature of 4°-10° C. for 24 hours or longer, as needs be, and a slow influx of oxygen during the preservation period. For extended period of time over 24 hours, the preservation solutions medium contains additional nutrients enabling the basal metabolism to proceed to assure the organ recoverability at the end of preservation period and before a transplantation.

The unique properties of the process are (a) perfusing or washing the organ with a first novel preservation solution containing a pyruvate, protein such as albumin or fetal calf serum and ethylenediaminetetraacetic acid (EDTA), at a warm, preferably room temperature, to remove blood and metabolites from the organ, to load the cells with pyruvate, and to increase the flow of the perfusate through the circulation; (b) serially perfusing the organ with a second novel preservation solution comprising the first solution and a small percentage preferably between 0.01-6%, most preferably around 0.1-4% of ethanol to bring about the reversible decrease in metabolism to the basal metabolic level, prevent edema and retain the integrity of the vascular bed, said perfusion also being performed at a temperature between 4°-37° C.; and (c) submerging the organ having cannulated primary incoming vein, when appropriate, to allow for diffusion of gases and preservation media, into the large volume of the first solution for the entire preservation period. The preservation step is maintained at temperature between 2°-10° C., preferably for at 4° C. for the entire period of the organ preservation.

Unique properties of the preservation solutions are: (a) a presence of pyruvate as a substrate for energy supply demands substituting for generally used glucose which leads to the metabolic acidity and edema causing the damage to the organ function; (b) a presence of protein such as albumin or fetal calf serum useful for tissue renewal; (c) absence of glucose as an energy source; (d) absence of phosphate to preserve energy; (e) a presence of EDTA used for removal of harmful ions; and (e) in case of the second preservation solution, the presence of ethanol to affect the reversible decrease in metabolism, prevent edema and retain the integrity of the vascular bed.

The combination of both novel sequential process and novel preservation solutions results in unique technology for preservation of the organs for transplantation for periods six or more time longer than known until now.

Design of Preservation Solutions

Successful preservation solution suitable for long-term preservation of the organ must protect the organ against deleterious effects of the long-term induced ischemia which results from the interrupted oxygen supply during the time when the circulation of the donor is stopped before or during the organ removal from the donor and until the organ is connected in the recipient's circulation which assumes and restores the oxygen-blood supply. Since it is well known that for many organs the ischemia extended over 20-30 minutes has often fatal consequences due to and irreversible damage to the organ, it is necessary to design either the preservation solution in such a way that it would prevent ischemia to occur, or to design a conditions which would allow ischemia to occur but would still assure that there is no irreversible damage to the organ and that, after the ischemic period, the organ can resume its normal physiological activity.

In designing the novel cardioplegic solution of this invention, ions are needed to retain the potential difference across the membrane but must be chosen carefully. Some Pi is needed, too much lowers the energy state. Some $Ca^{+2}$ is needed, too much results in increased work. Some $Mg^{2+}$ is needed, but too much competes with $Ca^{2+}$. Some KCl is needed but too much leads to vasoconstriction. Bicarbonate is needed to retain the pH in a physiological state. Sodium chloride is used to balance the osmolarity and retain the action potential across the cell membranes.

As has been discussed above, while the source of energy for the continuous organ activity is necessary even if the organ is in basal metabolic state, it has been found that glucose, which was predominantly used as a source of energy in currently available preservation solutions, causes the acidosis and edema of the tissue which subsequently result in the impairment of the normal function of the tissue. Glucose and fatty acids are more deleterious to the organ during ischemia due to build up of by-products including accumulation of sugar phosphates. Pyruvate, on the other hand is a beneficial substrate protecting the organs against ischemia, acidosis, edema and a calcium overload. These fundamental observations led to current formulation of a saline solution with pyruvate as the substrate and to the current finding that by substituting glucose in the preservation solution with pyruvate, the tissue acidosis and edema does not occur. Moreover when such solution is combined with alcohol as an agent to arrest the metabolism, a beneficial preservation solution suitable for long-term preservation of the organ results. The discovery described here indicates that using, in certain sequence, the preservation solution containing pyruvate, and pyruvate plus ethanol, is able to protect the organ's function for a 24 hour period or longer.

In the absence of work, the organs are able to survive in, and utilize, a basal energy state because there is normally an excess concentration of high energy phosphate present in the cells. It appears that when the organ is in a dysfunctional state, the diffusion of oxygen from the oxygenated media is sufficient to maintain the basal energy state of the organ. This occurs at a reduced energy level, but substrate still may be necessary to maintain a viable basal state. Consequently, when the suitable substrate, such as pyruvate, is provided and when the organ is introduced into the basal energy state by the alcohol, it is able to survive without substantial damage and impairment of its function for at least 24 hours or longer.

Advantages provided by this invention became readily apparent, since the previously known survival of the organs, while timewise differing, due to their functional disruption induced by the removal of the organ from the donor is only somewhere around 2-6 hours, at which time the organ needs to be placed in the recipient's circulation, or the irreversible damage or death of the organ occurs.

The organ preservation solution of this invention contains, per liter of deionized or distilled sterile water, 90 -120, preferably 17 mM (6.42 g) of sodium chloride, 4.0-4.5, preferably 4.3 mM (0.32 g) of potassium chloride, 0.5-2.5, preferably 2 mM (0.294 g) of calcium chloride, 22-28, preferably 25 mM (2.1 g) of sodium bicarbonate, 0-1 mM, preferably 0.5 mM (0.146 g) of ethylenediaminetetraacetic acid (EDTA), 1.0-2.0, preferably 1.2 mM (0.144 g) of magnesium sulfate or equivalent amount of magnesium chloride, 6-12, preferably 10 mM (1.1 g) of sodium pyruvate and 0.05-1%, preferably 0.1% of protein such as fetal calf serum or albumin such as synthetic or natural albumin or an other protein which will provide viscosity similar to the albumin.

Solution consists essentially of the first solution 1 with added 0.01-6% preferably 4% of lower alcohol, such as ethanol and may be used at temperatures from 4° C.-37° C. In alternative, alcohol may be substituted with additional 18-26 mM, preferably with 20 mM (1.3 g) of potassium chloride which can only be used of temperatures between 2°-8° C.

Both solutions may contain additionally 5-20% of fluorocarbon, such as perfluorocarbon obtained from Green Cross, Japan, preferably in emulsified form.

In another embodiment, the preservation solutions may additionally contain individual essential amino acids or mixtures thereof, or be completely substituted with Eagle or 199 media obtained, for example, from Gibco Laboratories.

Procedure for Organ Preservation

Figures 1A, 1B:
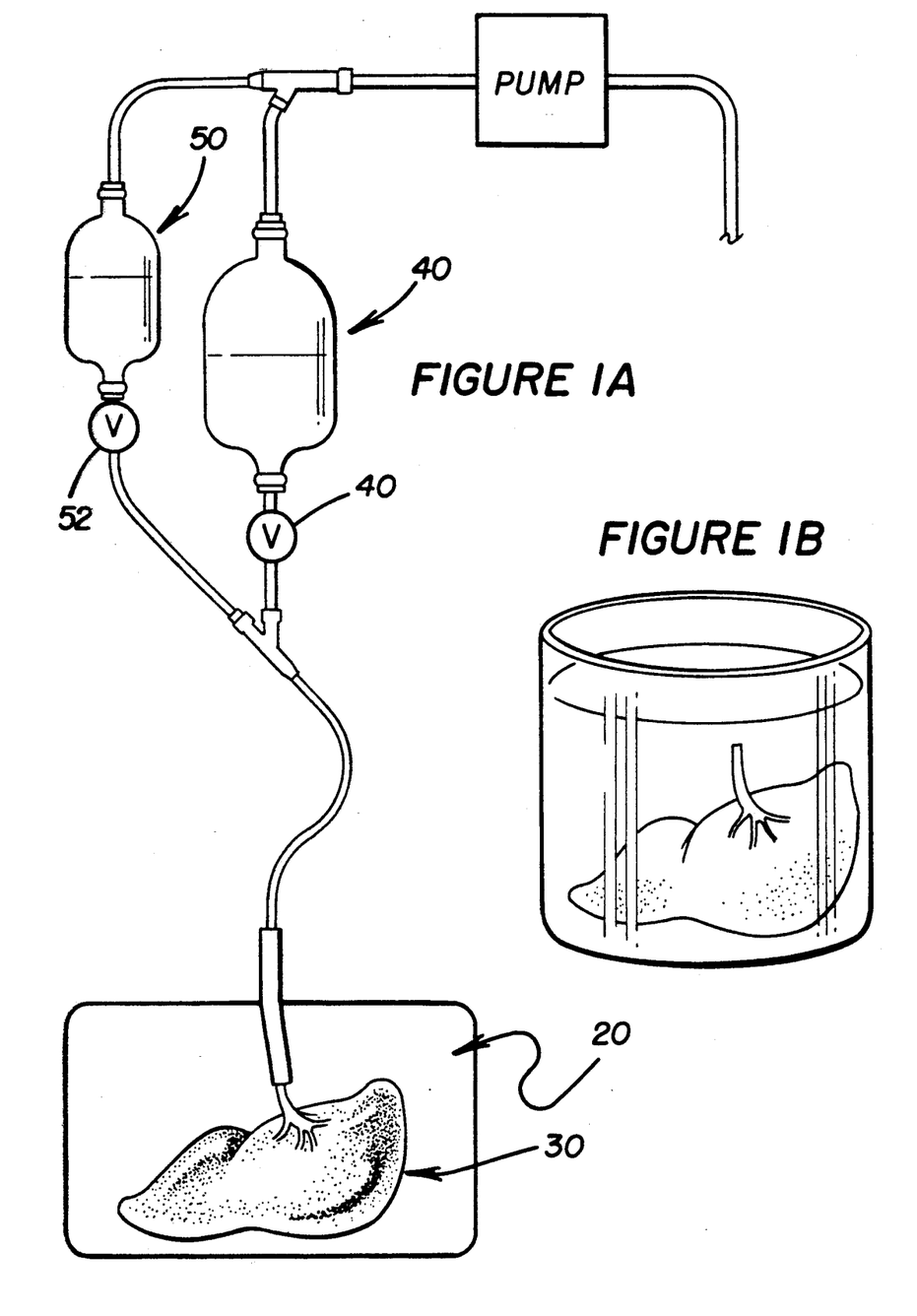
FIG. 1 is a diagrammatic representation of liver preservation conditions.

Liver 30, or any other organ with cannulated portal vein as shown in FIG. 1A is submerged in the perfusion chamber 20 and connected via cannula to container 40 containing solution 1 and container 50 containing solution 2, both being regulated with valves 42 and 52 respectively. Each container has build-in thermistor to enable to preset and maintain certain temperature. Perfusion by the solution 1 or 2 then proceeds. The perfusion with solution 1 containing pyruvate bypasses the glycolytic pathway. Glycolysis is slow in the cells. Glycolysis is partially rate-limited by phosphofructokinase, which is inhibited by intracellular calcium $[Ca^{2+}]i$ and hydrogen ions $[H^+]i$ and activated by cAMP. $[H^+]$ and $[Ca^{2+}]i$ are augmented in ischemia. When glucose was used as the only substrate, in the preservation solution [NADH]/[NAD], the phosphorylation potential and developed pressure were significantly lower and concentrations of phosphomonoester sugars and hydrogen ions $[H^+]i$ were significantly higher in isolated cardiomyopathic organs as compared to normal organs. Pyruvate on the other hand was shown to lower $[Ca^{2+}]i$. The results published in *Basic Res. Cardiol.*, (1990), suggest that ischemic failure is partially the result of calcium and/or hydrogen ion-induced inhibition of glycolysis, which is alleviated by bypassing the glycolytic pathway with pyruvate.

Consequently, the presence of pyruvate in the solution provides unique protection for the organ cells by preventing development of edema, ischemia, calcium overload, acidosis and preserve the cell action membrane potential across the membrane.

The organ is perfused with solution 1 for 1-20 minutes, preferably for about 10 minutes at a warm temperature between 28° C. to 37° C., preferably around 35°-36° C. At this temperature, the solution increases flow and loads the cells with an energy supply in the form of a clean substrate pyruvate and vasodilates the organ vessels as opposite to the cold cardioplegia which is known to cause vasoconstriction.

Cannulation of the incoming artery or vein allows the solution to circulate through the whole organ and thus provide exchange by diffusion of gas, substrate and media during perfusion and storage between the solution and the cells. At the end of perfusion with solution 1, the valve 42 is closed and the valve 52 is opened to allow perfusion with solution 2 containing alcohol. Solution 2 containing both pyruvate and 0.01-6% of alcohol, preferably 4% of ethanol, causes the arrest of the organs metabolism, vasodilation, and also inhibits the $Na^+/Ca^{2+}$ exchange by preventing the efflux of $Ca^{2+}$. A combination of low Na and ethanol lowers the influx of $Na^+$ during the calcium paradox and the efflux of $Ca^{2+}$. As a result the cell is not depleted of $Ca^{2+}$ during the calcium paradox and not loaded with $Ca^{2+}$ during repletion and the organ is able to recover from the calcium paradox during reperfusion when ethanol is present during the $Ca^{2+}$-depletion period. To assure a low $Ca^{2+}$ concentration during the $Ca^{2+}$-depletion period, 0.5 mM EDTA was added to the perfusate.

Perfusion with the second solution containing alcohol proceeds for 1-20 minutes, preferably around 10 minutes at temperatures from 2° C. to 37° C. Higher temperatures than 28° C. are preferred because they allow for vasodilation but when the circumstances require, the temperature may be lowered to about 4° C. which will further slow down metabolism but more importantly will cause certain degree of vasoconstriction. The perfusion with the cold solution containing potassium chloride is preferably done at low temperatures around 4° C.

In alternative, the organ preservation according to the procedure of this invention can be successfully accomplished by perfusion with solution 1 at warm temperatures (24°-37° C.) and by subsequent cooling of the solution 1 to temperatures between 2°-10° C., preferably to 4° C. This temperature is also used for the storage period for this procedure wherein the organ cannulated with cannula intact is transferred to the container depicted in FIG. 1b. The only requirements for the container are that it is tightly closed, filled with enough of solution 1 in such quantity, usually between 3-8 liters, which allows complete submerging of the organ with cannula in the solution, that the aseptic conditions can be preserved including the aseptic supply of gas, preferably oxygen/carbon dioxide 95/5%, and the temperature maintained around 4° C. In alternative, the container may be equipped with the perfusion pump and the organ may be continuously perfused with solution 1 at temperature between 2°-8° C., preferably around 4°

C. or any other temperature which is needed for its preservation.

Using the procedure of this invention, the organ may be successfully preserved from 24 hours to seven or more days provided that the constant supply of oxygen and essential energy substrate and nutrients is provided.

Additional agents, such as drugs, hormones, vitamins and other pharmaceutically acceptable excipients may be added to solution 1 or 2.

The feasibility of the novel preservation solutions for long-term organ preservation was studied on animal hearts, livers and kidneys. Isolated hamster hearts were first perfused with a normal Krebs-Henseleit or Langendorf medium to demonstrate comparable viability of hearts prior to perfusing and storing for 24 hours in one of three solutions. The same experimental conditions and solutions were used in studies on isolated rat kidneys.

The three solutions applied to three groups of hears are described in Example 1 and were: Solution (A) a physiological saline containing pyruvate as the substrate and 4% alcohol to arrest the organ's metabolism; Solution (B) a standard cardioplegic solution; and Solution (C) a physiological saline containing pyruvate as the substrate.

Figure 3A:
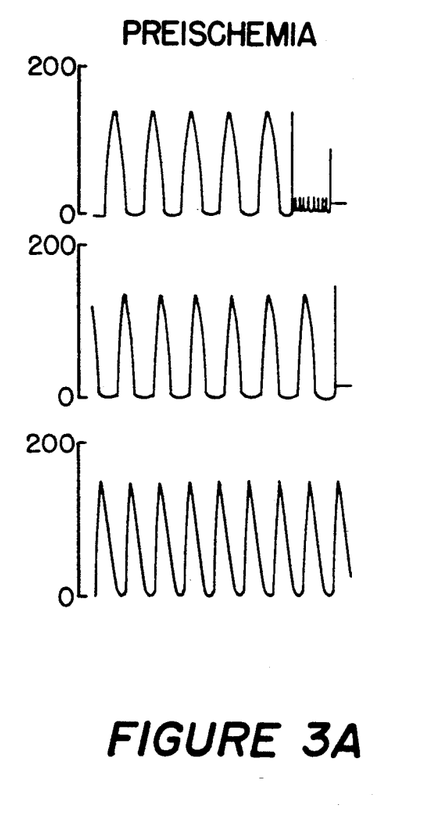
FIG. 3 depicts ventricular pressure for hearts perfused by cardioplegic solutions in pre-ischemic and postischemic hearts.
Figure 3B:
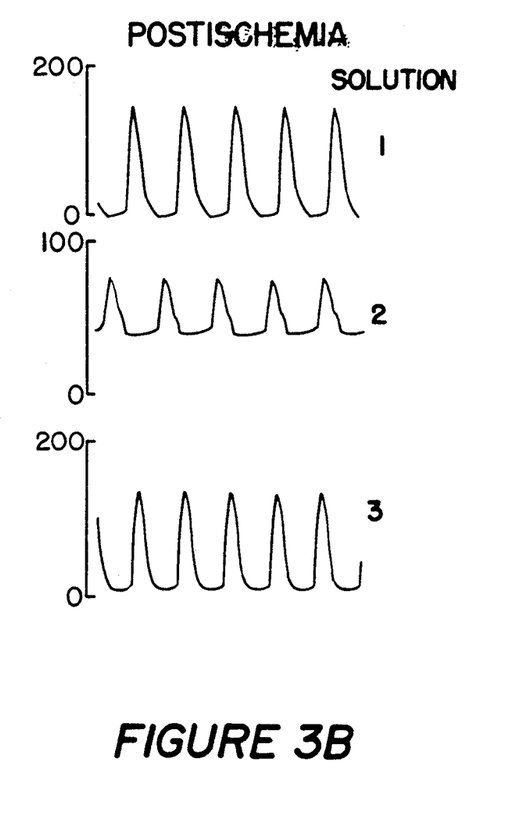

FIG. 3 shows a representative drawings of left ventricular pressure for hearts perfused in solutions A, B and C for baseline levels, called preischemia, and 30 minutes reperfusion following 24 hours of storage called postischemia in each solution at 4° C. For solution A, which includes pyruvate and 5% of ethanol, the preischemic and postischemic pressure is almost the same, i.e., the height of peaks is the same and only the rate of the contractions in postischemic heart in solution A is slower. Thus, this solution is able to preserve the pressure and the heart for 24 hours without any apparent impairment in cardiac function. This coincides with results summarized in Table I where the developed pressure and end-diastolic pressures are the same for pre- and post ischemia. Coronary flow and heart rate are somehow slower and the oxygen consumption is about the same. For solution C, containing pyruvate as a substrate results are similar. Although the height of the developed pressure in postischemia is not quite the same as in preischemia, during the contractions of the heart the pressure returns to 0 levels. Both end-diastolic pressure and coronary flow are the same with heart rate slower and oxygen consumption slightly lower in postischemia. Solution B, which has no pyruvate and no alcohol, shows drastical reduction in heart contractility, wherein the postischemic heart contracts only somewhere between 40-70 mm Hg instead of 0-160 as seen in preischemic heart. The results in Table I support these findings. Developed pressure, coronary flow, heart rate and oxygen consumption are all much lower, with end diastolic pressure much higher. This confirms that the heart stored in solution B is edemic and ischemic, probably due to too much of $Ca^{++}$ and lack of available energy substrate, and its function is only about 50%.

Figure 4A:
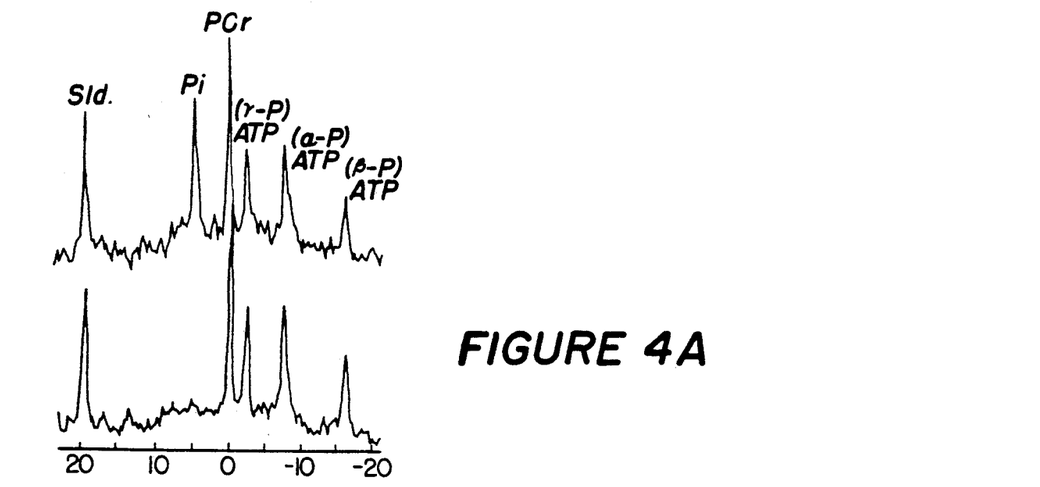
FIG. 4 depicts NMR spectra of hearts pre-ischemic and post-ischemic baseline energy level.
Figures 4B, 4C:
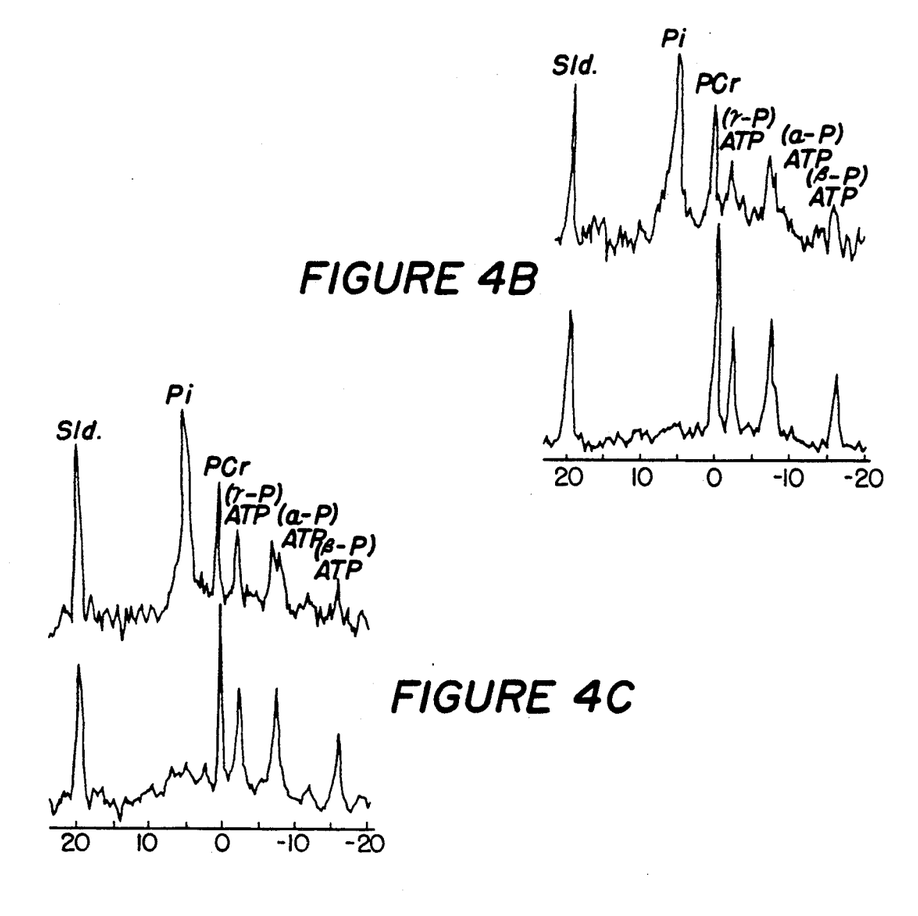
Figures 5A, 5B:
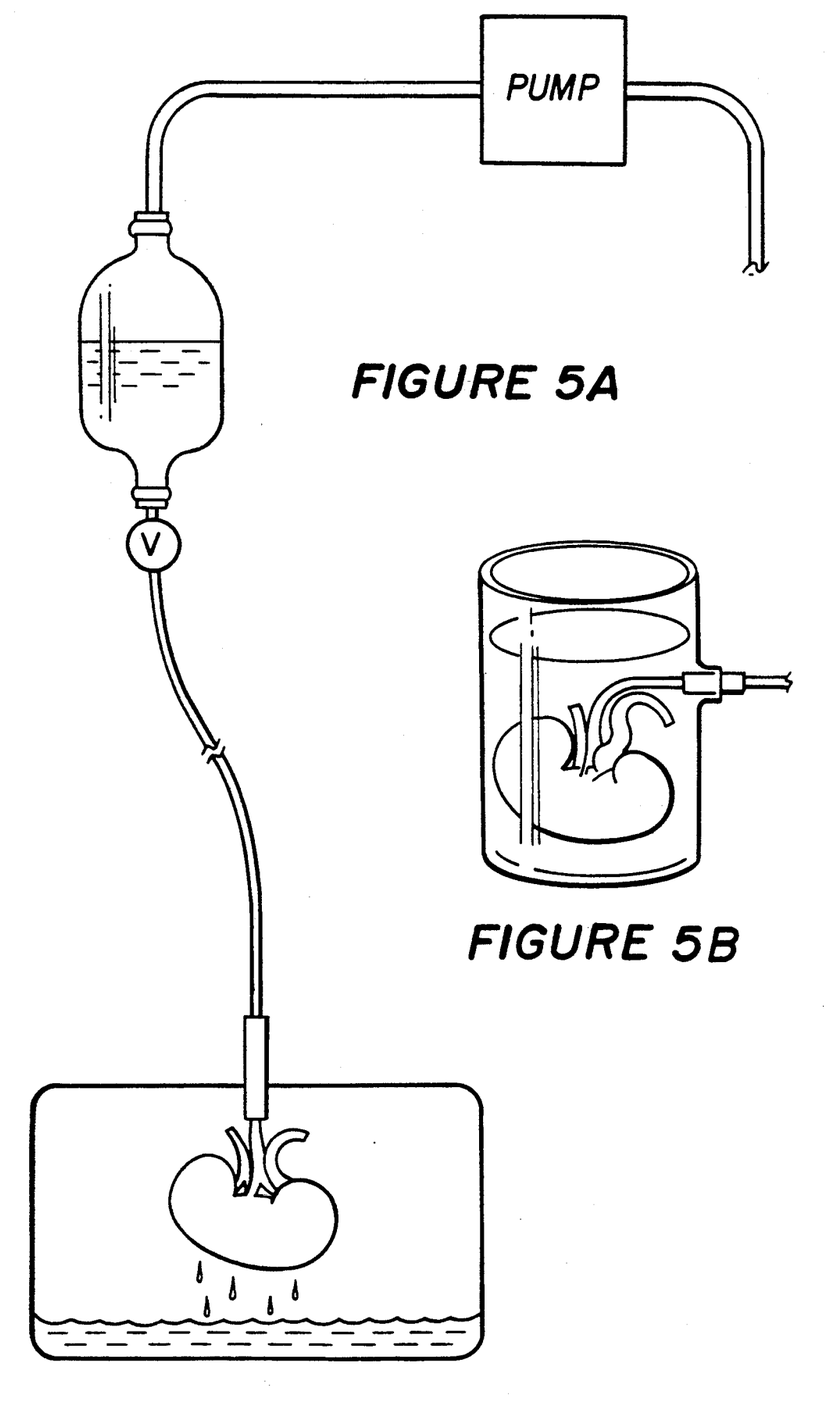
FIG. 5 is a diagrammatic representation of kidney preservation apparatus with continuous perfusion.

FIG. 4 A, B and C shows representative 31P-NMR spectra of hearts preischemic (baseline energy level) and postischemic (30 min reperfusion following 24 hours storage) for hearts perfused in solution (A), solution (B), and solution (C).

The upper lower spectra show the preischemic spectra, the upper spectra are postischemic. When the energy level is about the same, the spectra look the same. As seen from Spectra A, both upper and lower spectra are about identical, while spectra B, showing the energy level after 24 hours storage in Roe Standard solution, shows the presence of large amount of inorganic phosphate evidencing intracellular inequilibrium and intracellular acidity. ATP and creatinephosphate (PCr) are grossly diminished when the solution C was used without alcohol, depletion in energy supply is also seen because the heart was not put into the basal metabolic rate state and there was not sufficient supply of energy substrate to support full heart metabolism. The spectra in FIG. 4 are confirmed by results summarized in Table II.

In practice of this invention, the donor's heart, heart-lung complex, kidney, spleen, testicles, ovaries, pancreas, brain or liver are first cannulated as shown in FIG. 1, which depicts a diagrammatic representation of conditions for organ transplantation. The heart aorta and the left ventricle or portal, renal, splenic, pancreatico-duodenal veins, ovaries or spermatic artery are first cannulated, perfused with the warm physiological solution and hemodynamic measurements of baseline metabolic and physiologic levels are made. That state is herein called preischemia. The vascular pressure is measured. The organ is then excised and placed in the perfused working organ apparatus (FIG. 2) and the perfusion with the first preservation solution is started through the cannula connected to container 40 containing Solution 1 immediately. The perfusion continue for 2 to 60 minutes, preferably for about 5-10 minutes or until all remnants of the blood impurities or debris are washed out from the organ. When the rinsate is clear of blood, the cannular connection is switched to the container 50 with preservation solution 2 containing 0.01-6%, preferably 0.1-4% of ethanol. The amount of alcohol will depend on the organ. For example, liver and brain perfusate will contain only small amount if at all of alcohol. Both containers are kept at temperature between a room temperature to around 37° C., preferably at the temperature allowing the perfusing solution 1 and 2 to have a body temperature, i.e., of about 37° C. The solution 2 however, may be perfused at temperature 4° C. Nevertheless, a perfusion with colder temperatures as low as 2° C., preferably 4° C. is possible and contemplated to the within the scope of this invention.

The controversy connected with the applied temperature of a preservation solution has been discussed above and the detriments connected with freezing of organs or hypothermia are well documented. Although the most commonly used preservation solution is a cold potassium chloride solution, advantages of warm, oxygenated blood solution were described in *J. Thorac. Cardiovasc. Surg.*, 91:888 (1986). In this invention, perfusing the organ with solutions at warm temperature was found beneficial since it allowed flushing of the veins and organ vessels and prevented them from collapsing. It was also found to be important to remove all blood from the organ since the breakdown of hemoglobin releases, among other things, iron which may have deleterious effects o clotting and inhibition of enzymes.

The perfusion of the organ with the solution 2 effectively stops the organ work and induces the basal state. At this state, in which the organ is in the basal state, as evidenced by the diminished metabolism measured by biochemical techniques known in the art, and having canula/cannulae intact and opened, the organ is transferred to the storage container filled with solution 1 and maintained at temperature between 2° C.-10° C., preferably about 4°-15° C. Container can be of any size and shape as long as it contains at least 4-8 liters of solution 1 so that the cannulated organ including open ends of canulae are submerged at all times in the solution 1. One example of such container is shown in FIG. 1(b). It is important that the container are that is tightly capped and is equipped to provide slow but continuous influx of oxygen. The container and a solution therein must both be sterile and the influx of oxygen must be done aseptically. The cannulation tubes are provided and are necessary for continuous aeration by diffusion of the cell and tissues while in the storage container. The cannulation tubes are designed so that the physician performing transplantation can connect the cannula to a pressure transducer in order to check pressure in the organ or other parameters before transplanting.

Tightly closed container is connected to a transportable miniature oxygen supply and is transported and transportable anywhere in the whole world by any means of transportation, and as long as it the container not submitted to excessive heat or cold which would damage organ tissue, it can be stored for at least 24 hours or more and the organ can be transplanted without loss of function. Following the properly done transplantation, the isolated organ for transplantation will regain 90-100% of its normal physiological function and around the 70% of its cellular metabolic activity immediately upon connecting the organ to the recipient's circulation.

Figure 2:
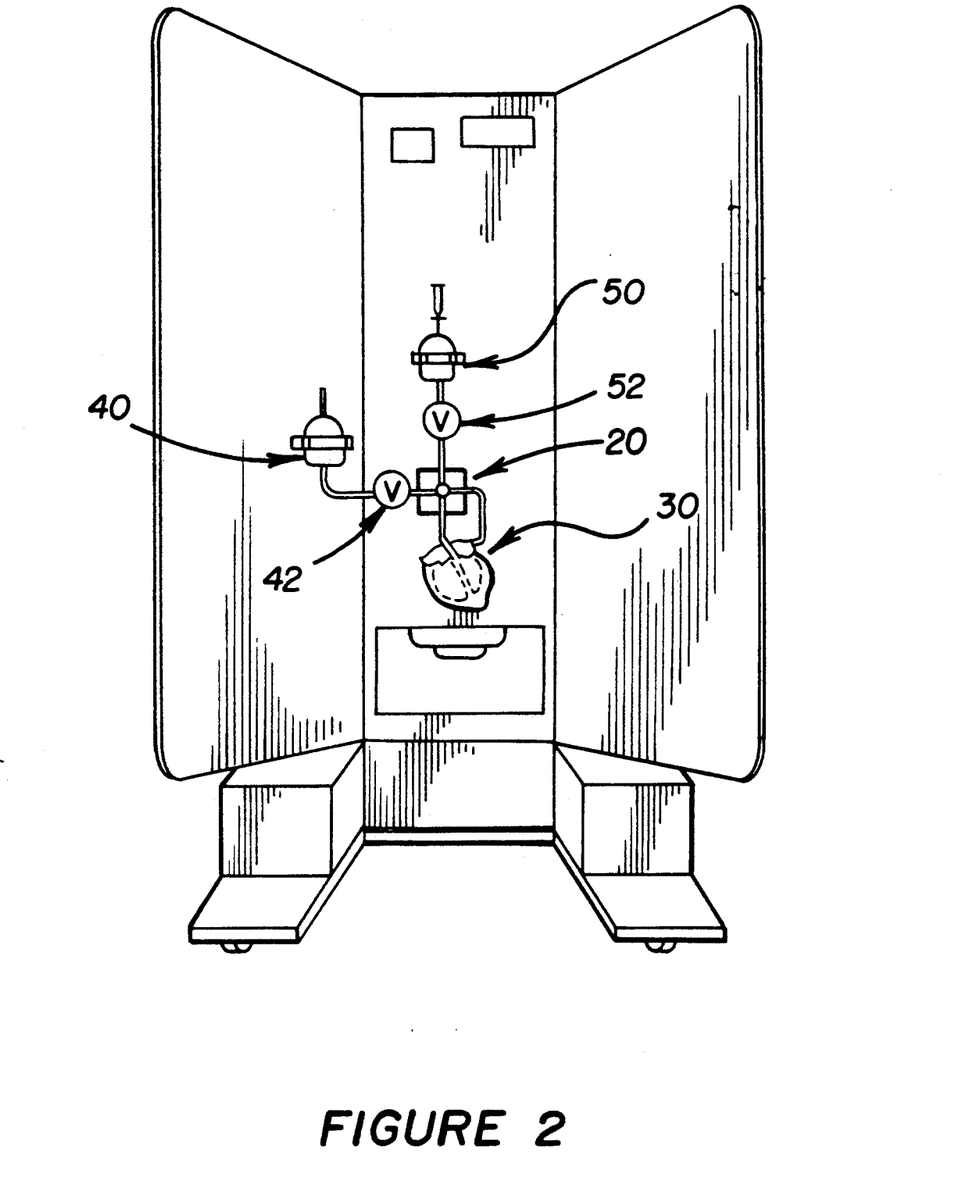
FIG. 2 is the model of apparatus for perfusion of the organ.

All organs which can be transplanted are contemplated to be within the scope of this invention. The heart, heart-lung complex, liver, kidney, spleen and pancreas are first cannulated, if possible, in-situ, in the donor's body via any major vein. Then the organ is gently removed under the strictly aseptic conditions accepted in the surgical procedures and the first rinsing of the organ with the warm physiological solution is quickly done. Then the organ, with canula/canulae intact, is quickly removed and transferred to the isolated organ apparatus, as shown in FIG. 2, wherein the organ is preferably submerged in the solution with which it is perfused, to prevent drying of the organs surface. In another arrangement, the organ apparatus has enclosed humidified chamber where the organ is hanging or laying on the surface of the supporting structure throughout the perfusion period with solution 1 (2-10 minutes) and solution 2 (2-20 minutes), in series. After the basic biochemical and functional tests have been performed, but immediately after the end of the perfusion with the solution 2, the organ is gently transferred into storage container and submerged completely including the end of cannula/cannulae in the solution 1 again and stored for 24 hours or more at low temperature of about 2°-10° C., preferably 4° C.

In alternative, the organ is first perfused with a warm solution 1 (35°-37° C.) and when all blood and tissue debris is rinsed out, the perfusate is cooled down and the organ is stored, as above, in the cold solution 1 at temperature of 4° C. In yet another alternative, the organ is first perfused with solution at warm temperature and then transferred into cold solution 2 at about 4° C. Optionally, oxygen carriers such as various fluorocarbons, for example perfluorocarbon in amount from 5-20% can be added to the solution 1, 2 or both. In this instance, the fluorocarbon will be emulsified with for example lecithin, using methods known in the art.

Another alternative contemplated to be within preview of this invention is the replacement of the solution 1 or solution 2 with the liquid media, such as Medium 199, available from GIBCO Laboratories, N.Y., which consist of mixture of essential amino acids, as long as the medium is either mixed with or prepared with the pyruvate in amount from 1-20 mM, preferably in amount 6-12 mM. These medium/pyruvate solutions will be particularly useful for preservation of organs for longer than 24 hours period of time and mainly for preservation of heart, heart-lung, brain and embryo.

In yet another alternative, the solution 1 or medium/pyruvate combination may be used for continuous perfusion of the organ in the storage chamber. In such practice a portable miniature perfusion pump is connected to the container aseptically and connected to the cannulated organ. The medium/pyruvate on the solution 1 or 2 are then continuously perfused for the whole period of preservation and storage.

Tightly closed container is connected to a transportable miniature oxygen supply and is transported and transportable anywhere in the whole world by any means of transportation, and as long as it is not submitted to excessive heat or cold which would damage the organ tissue, it can be stored for at least 24 hours or more and transplanted without loss of function. Following the properly done transplantation, the isolated organ for transplantation will regain 90-100% of its normal physiological function and around the 70% of its mitochondrial activity immediately upon connecting the organ to the recipient's circulation and can survive in the preservation solution of this invention from 0 hours to 7 days.

Surgical techniques may need to be altered in order to prevent CNS dysfunction during reperfusion of the implanted donor organ containing the 4% ethanol or the preserved organs would need to be reperfused in a solution containing pyruvate prior to implanting, in order to remove ethanol.

Use of alcohol as a preservation solution may have limited use for transplantation unless the alcohol is perfused out of the organ system prior to use. Thus, it is contemplated to be advantageous to store the organ in the physiological saline containing pyruvate but not alcohol. However, functional recovery in the latter is still better than a standard preservation solution.

UTILITY

This invention is useful for organ transplantation, in particular for the transplantation of organs which require, beside suitable preservation solution, also special conditions in order to preserve their physiological function. The invention process is equally suitable for 24 hours preservation of the organ prior to the transplantation as it is suitable for longer than 24 hours preservation of the organ. In such an event, there will be continuous supply of pyruvate and/or other nutrients, whether added to the solutions of this invention or supplied by the medium 199 which contains pyruvate, ions and other agents needed for such extended survival. These extended preservation periods are within the scope of this invention. Various drugs and agents such as hormones, vitamins, nutrients, antibiotics and such others may be added to preservation solutions at any stage of the protective process of this invention as long as the aseptic conditions and safety are maintained.

The following examples are intended to illustrate the invention. They should not be in any way interpreted to limit the scope of this invention.

EXAMPLE 1

Preparation of Cardioplegic Solutions

This example illustrates preparation of cardioplegic solutions for long-term preservation of heart for transfusion.

Solution A 1.07 mM (6.25 g) of sodium chloride, 4.3 mM (320 mg) of potassium chloride, 2 mM (294 mg) of calcium chloride, 25 mM (2.1 g) of sodium bicarbonate, 0.5 mM (146 mg) of sodium EDTA, 1.2 mM (144 mg) of magnesium sulfate, 10 mM (1.1 g) of sodium pyruvate, 0.1% 1 of fetal calf serum and 4% of ethanol were dissolved at room temperature under constant stirring in 1 liter of deionized distilled sterile water, pH was adjusted to 7.4, and the solution was stored in the refrigerator at 4° C. until used for heart perfusion.

Solution B 20 mEq/l of potassium (K+), 27 mEq/l of sodium (Na+), 3 mEq/l of magnesium (Mg 2+), 47 mEq/l of chloride (Cl−) was dissolved in 1 liter of deionized water. The solution was adjusted to osmolarity 347 and pH 7.6 and stored at 4° C. in the refrigerator. The preparation of this solution is described in *J. Thorac. Cardiovasc. Surg.*, 73:366 (1977).

Solution C 1.07 mM (6.25 g) of sodium chloride, 4.3 mM (320 mg) of potassium chloride, 2.0 mM (294 mg) of calcium chloride, 1.2 mM (144 mg) of magnesium sulfate, 25 mM (2.1 g) of sodium bicarbonate, 0.5 mM (146 g) of Sodium EDTA and 10 mM (1.1 g) of sodium pyruvate were dissolved, under constant stirring in 1 liter of deionized water, pH was adjusted to 7.4, and the solution was stored at 4° C. in the refrigerator. Before use, solutions were oxygenated with mixture of 95/5% of oxygen/carbon dioxide.

EXAMPLE 2

Testing of Cardioplegic Solutions

This example illustrates testing and effect of cardioplegic solutions on the heart preservation.

Animal hearts were obtained from Golden hamsters weighing approximately 140 grams and 18 months of age. The animals were anesthetized with ether. After midline sternotomy the heart was rapidly excised with removal of the pericardium, immediately connected to an aortic perfusion cannula and perfused by a modified Langendorff method described in *Am. J. Physiol.*, 245:H 354 (1983) with a perfusion pressure of 140 cm $H_2O$. The oxygenated perfusate was equilibrated with 95% $O_2$ and 5% $CO_2$. All hearts were first perfused with a physiological saline [117 mM NaCl, 4.3 mM KCl, 2.0 mM $CaCl_2$, 1.2 mM $MgCl_2$, 0.1 mM $K_2HPO_4$, 25 mM $NaHCO_3$, 0.5 mM NaEDTA, 15 mM glucose, and 10 units/liter insulin.] After 15 minutes equilibration physiological measurements were made and energy metabolites were studied.

Physiological measurements included oxygen consumption, $pO_2$, and coronary flow. Oxygen consumption was determined as follows: Arterial samples were aspirated from the aortic chamber and venous samples were drawn from a catheter introduced into the right ventricular outflow tract for oxygen measurements (Corning model 165/2 gas analyzer). $PaO_2$ was measured and the oxygen content calculated as the product of coronary flow and coronary oxygen extraction. Coronary flow was determined by collecting the effluent of the right ventricle for one minute. A cannula was inserted through the left atrial appendage and into the left ventricular cavity, connected to a Statham P23Db pressure transducer.

Magnetic resonance spectroscopy was performed as follows. $31_p$ magnetic resonance spectroscopy of the beating isolated perfused heart was obtained on a 5.6 Tesla vertical 76 mm bore magnet as described in Circ. Res., 59:597 (1986). $31_p$ NMR spectra were obtained without proton decoupling at 97.3 MHz, using a 1180 Nicolet computer, a pulse programmer, and a high resolution 20 mm broad-band probe. Pulse angle was 60° C., recycle time 1.25 sec, and spectra width 4000 Hz. The 512 transients were accumulated during a 10 minute period. The signal to noise ratio was approximately 30:1. To correct for partial saturation, fully relaxed spectra were obtained at 15 second recycle time, and correction factors for phosphocreatine (PCr) and intracellular phosphate (Pi) were determined (3% and 5% respectively). Chemical shifts are referred to the resonance position of PCr. The peaks characteristic peaks of intracellular phosphate, phosphocreatine and phosphate groups of adenosine triphosphate (ATP) were identified. Intracellular pH was standardized as follows: A standard solution at physiological ionic strength (150 mM KCl, 8 mM ATP, 10 mM PCr, 5 mM Pi, and 9 mM $MgSO_4$) was used at a temperature of 37° C. to obtain the chemical shift titration curve of pH dependent Pi to PCr peak difference; this curve was fitted to the Henderson-Hasselback equation. Phosphate peaks were quantitated using manual electronic planimetry and estimated for whole heart detection by comparison to a capillary tube of standard methylene diphosphonic acid fixed inside the NMR tube. High energy phosphate values determined by −P-NMR were standardized by parallel studies of high pressure liquid chromatography of freeze-clamped tissue *Cardiovasc. Res.*, 20:471 (1986).

After the hearts were perfused with a Krebs-Henseleit solution physiological as well as biochemical measurements performed, the heart was transferred to solution A, solution B or solution C as described in Example 1.

The hearts were perfused for 10 minutes with one of the three solutions. Then, the cannula feeding the aorta was clamped, the cannulae leading to the aortic perfusate and to the pressure transducer were disconnected, and the heart submerged in one of the three respective solutions at 4° C. The details are depicted in FIG. 1. It was important that both cannulae were open during the 24 hours of storage for interchange with perfusate and dissolve $O_2$ in the perfusate. It was also important that no air entered the chamber during this time. After 24 hours of storage at 4° C., the cannulated hearts were again reperfused in a normal Krebs Henseleit medium. For reperfusion the cannula leading to the submerged aorta was clamped and placed in position of the perfusion apparatus. The cannula leading to the left ventricular chamber was again fastened into position.

The stimulator-triggered freeze clamp was attached to the perfusion apparatus. The pneumatic cylinders were driven at 60 Psi for "smashing" the heart and inducing a drop in temperature of the center of the heart from 37° to −80° C. in 5 msec. The frozen wafer anvils into liquid nitrogen when the cylinders were retracted using the neutralized extract, high energy phosphates were analyzed by high pressure liquid chromatography as described in detail in *IEEE Trans. Biomed. Eng.*, 29:448 (1982). The nucleotide were separate Beckman HPLC with a C-18 reverse phase column. All values were analyzed within a range of linearity.

Data are reported as mean and standard deviation. The unpaired Student t-Test was used for assessing the null hypothesis, and rejected at 95% confidence level.

EXAMPLE 3

Preischemic and Postischemic Cardiac Function

This example illustrates the preischemic and postischemic cardiac function depending on the cardioplegic solution used.

Three groups of isolated hamster hearts were perfused for 10 minutes with a Krebs-Henseleit solution according to procedures described in Example 2 and the base level (preischemia) of developed pressure expressed in mm HG measured in the left ventricle, end of diastolic pressure expressed in mm Hg, coronary flow expressed in ml/minute, heart rate expressed in beat/minute, rate pressure product $\times 10^3$ and oxygen consumption expressed in umoles/g/dry weight/minute was determined. Then, the hearts were perfused with one of the solutions listed in Example 1 as follows: Group I (6 hearts) was perfused with Solution A containing pyruvate and ethanol; Group II (6 hearts) was perfused with Solution B standard cardioplegic solution; and Group III (6 hearts) was perfused with Solution C containing pyruvate. The perfusion lasted about 10 minutes.

The hearts were then submerged for 24 hours in one of the three solutions described in Example 1. Both canulae were left open to assure the interchange with the perfusate solution and the supply of oxygen from the perfusate via cannulae into the heart. The ischemic period was 24 hours. After 24 hours of storage at 4° C., the cannulated hearts were again reperfused with a normal Krebs-Henseleit medium.

Preischemic, postischemic and control values were then determined and are summarized in Table I.

Preischemic and postischemic cardiac function is shown in Table I for all three groups. Prior to ischemia, among all three groups there was no significant difference in developed pressure, end-diastolic pressure, coronary flow, heart rate and consumption prior to ischemia. In postischemia as compared to preischemia, Group I showed no significant difference in developed pressure, end-diastolic pressure and oxygen consumption, however, there was a small but significant ($p<0.05$) decrease in coronary flow, heart rate and the rate-pressure product. Group II, on the other hand, showed a significant ($p<0.01$) decrease in all measured hemodynamic parameters, except end-diastolic pressure; in latter there was a significant ($p<0.001$) increase in pressure. In Group III there was a significant ($p<0.01$) decrease in heart rate, rate-pressure-product, and $O^2$ consumption, but no significant change in developed pressure, coronary flow and end-diastolic pressure. Between Groups I and III, there was no significant difference in end-diastolic pressure, coronary flow, developed pressure and heart rate, postischemically, however the rate-pressure-product and $O_2$ consumption were moderately but significantly smaller ($p<0.05$) in Group III as compared to Group I. Group II postischemically had a significantly ($p<0.01$) lower developed pressure, coronary flow, rate-pressure-product and $O^2$ consumption as compared to Groups I and III, and a significantly ($p<0.001$) higher end-diastolic pressure. Representative tracing of left ventricular pressure for hearts perfused in Solution A, B, and C are shown in FIG. 2 for preischemia (baseline level) and after 30 minutes of reperfusion following the 24 hours of storage (postischemia).

Recovery, based on the rate-pressure-product and oxygen consumption after 30 minutes of reperfusion was 81% and 93%, respectively for Group I, 13% and 32% for Group II, and 70% and 72% for Group III. Percent of physiological recovery was not related to recovery of ATP.

Retention of the heart in a cold cardioplegic solution was necessary in order to maintain the basal energy state of the heart low. There was an interchange of metabolites and oxygen with the coronaries and ventricular chamber. If the heart was not cannulated, as described, the heart could only survive for a few hours. If the aortic cannula was clamped closed, survival time was 60–90 minutes. Cardiac function was better preserved in hearts perfused with a saline solution cardioplegic containing alcohol and pyruvate as compared to the standard cardioplegic solution.

TABLE I

|  | I | II | III | IV | V | VI |
|---|---|---|---|---|---|---|
| GROUP I [N = 6] (Modified Krebs-Henseleit Medium) 5% Alcohol and Pyruvate as the substrate Solution A | | | | | | |
| Preischemia | 155 ± 16 | 2 ± 1 | 11 ± 1 | 218 ± 9 | 34 ± 2 | 39 ± 3 |
| Postischemia | 148 ± 13 | 2 ± 1 | 8 ± 2 | 184 ± 11 | 28 ± 2 | 37 ± 2 |
| GROUP II [N = 6] Roe's Cardioplegic Solution B | | | | | | |
| Preischemia | 148 ± 12 | 2 ± 1 | 11 ± 1 | 215 ± 8 | 32 ± 1 | 38 ± 1 |
| Postischemia | 55 ± 11 | 65 ± 8 | 5 ± 2 | 150 ± 12 | 4 ± 1 | 12 ± 2 |
| GROUP III [N = 6] (Modified Krebs Henseleit Medium) Pyruvate as the substrate and no alcohol Solution C | | | | | | |
| Preischemia | 156 ± 9 | 2 ± 1 | 10 ± 1 | 210 ± 9 | 33 ± 1 | 35 ± 4 |
| Postischemia | 134 ± 13 | 2 ± 1 | 10 ± 2 | 173 ± 12 | 23 ± 2 | 25 ± 3 |

I is developed pressure in mm Hg
II is end diastolic pressure mm Hg
III is coronary flow ml/min
IV is heart rate (BPM)
V is rate pressure product [$\times 10^3$]
VI is Oxygen consumption $\mu$ moles/g/day weight/min

EXAMPLE 4

Preischemic and Postischemic Energy Levels

This example illustrates the preischemic and postischemic energy levels depending in the cardioplegic solution used.

In the same three groups of isolated hamster hearts as described in Example 3, levels of ATP, phosphocreatine, inorganic phosphate [Pi] and intracellular pH [pH]$_2$ were determined. The results are summarized in Table II.

Preischemic and postischemic energy levels are shown in Table II. It was necessary to measure preischemic energy levels by $^{31}$P-NMR which is non-invasive so that the hearts would be available for further study. Standardized values obtained from $^{31}$P-NMR matched freeze clamped data. The NMR values were normalized and then standardized by parallel freeze clamped data. It was necessary to freeze-clamp in order to obtain the postischemic values since the energy levels were low at this time and difficult to detect by $^{31}$P-NMR in the small hamster hearts (approximately 0.6 grams). It was possible, however, to obtain the inorganic phosphate and [pH]$_i$ form the $^{31}$P-NMR data. The inorganic phosphate did not rise excessively high since there was no added phosphate in the perfusate. Preischemically there was no significant difference in the energy metabolites among the three groups of animals, nor any difference in [pH]i. Postischemically there was no significant difference in ATP and P$_i$ among the three groups of animals (Table II). On the other hand, PCr was significantly higher in Groups 1 (p<0.001) and 3 (p<0.01) as compared to Group 2. There was no significant difference in [pH]$_i$ between Groups 1 and 3, however the [pH]i was significantly more alkaline in Group 2 (p<0.05) (Table II). Representative $^{31}$P-NMR spectra are shown in FIG. 3 for baseline (preischemia) level and reperfusion following 24 hours of storage (postischemia) for hearts perfused and stored in Solution (A), Solution (B), and Solution (C).

The ATP level returned to approximately 40% of control level in all three groups, and in all three groups inorganic phosphate remained approximately 320% over control level after 30 minutes of reperfusion. Phosphocreatine was significantly higher in Groups 1 and 3 as compared to Group 2, related to improved oxygen consumption. Intracellular pH (pH)i, based on $^{31}$p-NMR, was physiological in Groups 1 and 3 but alkaline in Group 2. The latter may have been due to leaky membranes. Pyruvate helped to preserve mitochondrial function during depressed oxygen delivery, i.e., during 24 hours storage while 4% alcohol arrested the heart, and along with pyruvate was best for preserving functional recovery.

Alterations in the function of cardiac cellular membranes, which control the electrophysiological and mechanical behavior of cardiac muscle, may contribute to the pathogenesis of abnormal cardiac function. Alcohol affects transmembrane ion fluxes of Na$^+$, K$^+$, Ca$^{2+}$, and Cl and inhibits the Na$^+$/K$^+$ and the Na$^+$/Ca$^{2+}$ exchange, thereby reducing energy dependent processes during the basal state. Alcohol further decreases intracellular Na$^+$ levels, causes dehydration of the myocardial fiber and prevents edema.

As can be seen from the results retention for cardiac function was not related to ATP concentrations, Pi levels, or [pH]i. It is possible that the saline solution containing pyruvate and alcohol helped to maintain membrane integrity by influencing ion distribution. Upon reperfusion the hearts reperfused with Roe's cardioplegic solution had a slightly alkaline [pH]i. The latter may be due to leaky membranes and inability of the myocardial fibers to maintain the ion gradient. Rapid reversibility of cardiac depression is a desirable feature of a cardioplegic solution. The 4% alcohol caused an immediate arrest and the cardiac depression induced by alcohol was immediately reversible. An immediate arrest may not be crucial for preserving cardiac function since myocardial recovery was nearly as good with the physiological saline having pyruvate as the substrate, as compared to the same solution plus alcohol, and significantly better than a standard cardioplegic solution.

High intracellular calcium [Ca$^{2+}$]i and low [pH]i, which occurs with ischemia, inhibits glycolysis and fatty acid oxidation, resulting in accumulation of intermediates with no provision for synthesis of high energy phosphates. With reperfusion the PCr levels rose in the hearts of the groups which were provided pyruvate. Commensurate with the rise in PCr there was also an increase in oxygen consumption. Inorganic phosphate did not rise excessively high in any of the three groups; the latter is most likely due to the fact that no inorganic phosphate was added to the media.

The results of this study confirm that a saline solution containing 4% ethanol and 10 mM pyruvate preserves cardiac function over a 24 hour period, and that a saline solution containing 10 mM pyruvate partially preserves cardiac function over a 24 hour period.

TABLE II

|  | ATP (mM) | PCr (mM) | Pi (mM) | [pH]i |
|---|---|---|---|---|
| GROUP I [N = 6] (Solution A) 5% Alcohol and Pyruvate as the substrate | | | | |
| PREISCHEMIA | 9.8 + 1.2 | 11.9 + 1.1 | 3.6 + 0.4 | 7.05 + .02 |
| POSTISCHEMIA | 3.8 + 1.1 | 8.6 + 1.4 | 10.4 + 0.9 | 6.95 + .03 |
| GROUP II [N = 6] (Solution B) Roe's Cardioplegic Solution | | | | |
| PREISCHEMIA | 10.1 + 0.8 | 12.2 + 2.1 | 3.3 + 1.0 | 7.01 + .02 |
| POSTISCHEMIA | 4.2 + 0.9 | 3.2 + 1.2 | 9.6 + 1.4 | 7.22 + .07 |
| GROUP III [N = 6] (Solution C) Pyruvate as the substrate and no alcohol | | | | |
| PREISCHEMIA | 9.7 + 1.2 | 11.8 + 2.1 | 3.8 + 0.8 | 7.02 + .03 |
| POSTISCHEMIA | 3.6 + 2.1 | 6.2 + 1.4 | 11.8 + 1.4 | 6.97 + .06 |

EXAMPLE 5

Isolated Pig Heart Preserved for 24 Hours

This example illustrates the utility of the present invention for the preservation of the isolated heart of the higher mammal species.

Pig heart was precannulated as described before and removed from the pig's chest according to procedures described in Example 2. Preischemic measurements were done to determine levels of the same parameters for cardiac function and energy level as in Example 3. Then the heart was perfused for 15 minutes with cardioplegic Solution C and 10 minutes with cardioplegic Solution A. Both perfusions were done at 37° C. The isolated heart was then submerged in a 2 gallon container tightly closed and filled with the Solution 3 for 24 hours at a temperature 4° C. The heart, including cannulae was completely submerged in the Solution 3 which was continuously gently oxygenated with a mixture of 95% of $O_2$ and 5% of $CO_2$. All conditions were kept aseptic and the apparatus was sterilized beforehand. The heart was attached gently to the wall of the container wall so that no mechanical damage occurred during the simulated transportation from the one room to another. After 24 hours, the heart with both cannulae was removed from the container, reattached to the isolated heart apparatus and reperfused with the solution 3 again. The vital signs were followed.

At that time, more than 90% of the normal cardiac function of the myocardium and more than 70% of the mitochondrial activity was restored, measured by pressure, heart beat, coronary flow and ECG and $-P$-NMR.

EXAMPLE 6

Preservation of Isolated Liver for Transplantation

This example illustrates the long-term preservation of liver for transplantation.

A. The portal vein and the bile duct of the rat liver are cannulated, removed, transferred to perfusion chamber and perfused 10 minutes with the physiologic solution at 37° C. The perfusion is then switched to the solution A described in Example 1 and perfused for 10 minutes at 37° C. temperature for another 10 minutes. Samples and the level of transaminases are determined to show the degree of liver function. After 10 minutes, the perfusion is disconnected and the liver are submitted to $^{31}P$-NMR analysis as described in Example 2.

Liver is then transferred to the storage container filled with solution A and maintained at 4° C. as shown in FIG. 1B. Care is taken that the portal cannula is completely submerged.

Prior to the organ transfer, the container is preoxygenated with filtered mixture of oxygen and carbon dioxide 95/5% from the gas tank source kept outside of container. The container and the solution are kept aseptic at any time.

The liver are gently submerged in the solution A and stored for 24 hours. After 24 hours, liver is removed and the biochemical, enzymatic tests are performed and physiological function is determined by using $-P$-NMR.

B. The liver are treated with solution A and B in the same way as described in A.

Storage container connected with the attached portable perfusion pump is prepared as in A and the liver is connected via the portal cannula to the perfusion pump. Perfusion is maintained at steady rate of 4 ml per minute. The production of bile is followed as one of the sign of normal functional capability. The perfusion is done at 4° C. with the solution A.

C. The liver are treated as in A but storage solution A contains 10% of emulsified perfluorocarbon.

D. The liver are treated as in B but storage solution A contains 10% of emulsified perfluorocarbon.

E. The liver are treated as in A by it is perfused first with solution A at 37° C. for 10 minutes, then the temperature is dropped to 4° C. and then the liver is transferred to storage container and stored at 4° C. in solution A for 24 hours.

Under all the above conditions, the liver retains its functional and anatomical integrity as evidenced by the biochemical tests and by $^{31}P$-NMR for more then 7 days.

EXAMPLE 7

Preservation of Isolated Kidney for Transplantation

This example illustrates the long-term preservation of kidney for transplantation.

A. The renal vein of the rat kidney is cannulated, removed, transferred to perfusion chamber and perfused 10 minutes with the physiologic solution at 37° C. The perfusion is then switched to the solution A described in Example 1 and perfused for 10 minutes at 37° C. temperature for another 10 minutes. After 10 minutes, the perfusion is disconnected and the kidney is submitted to $^{31}P$-NMR analysis as described in Example 2 for determination of functionality.

Kidney is then transferred to the storage container filled with solution A and maintained at 4° C. as shown in FIG. 1B. Care is taken that the renal cannula is completely submerged.

Prior to the organ transfer the container is preoxygenated with filtered mixture of oxygen and carbon dioxide 95/5% from the gas tank source kept outside of container. The container and the solution are kept aseptic at any time.

The kidney is gently submerged in the solution A and stored for 24 hours. After 24 hours, kidney is removed and the biochemical, enzymatic, and physiological functions are determined by using $^{31}P$-NMR and other tests known in the art.

B. The kidney are treated in the same way as described in A.

Storage container connected with the attached portable perfusion pump is prepared as in A and the kidney connected via the renal cannula to the perfusion pump. Perfusion is maintained at steady rate of 3 ml per minute. The perfusion is done at 4° C. with the solution A.

C. The kidney is treated as in A but storage solution A contains 10% of emulsified perfluorocarbon.

D. The kidney is treated as in B but storage solution A contains 10% of emulsified perfluorocarbon.

E. The kidney is treated as in A by perfusing it first with solution A at 37° C. for 10 minutes, then the temperature is dropped to 4° C. and the kidney is transferred to storage container and stored at 4° C. in solution A for 24 hours.

Under these conditions, the kidney retain its functional and anatomical integrity as evidenced by the biochemical tests and by $^{31}P$-NMR for about 5 days or longer.

EXAMPLE 8

Preservation of Isolated Spleen for Transplantation

This example illustrates the long-term preservation of spleen for transplantation.

A. The splenic artery of the rat spleen are cannulated, and the spleen is removed, transferred to perfusion chamber and perfused 10 minutes with the physiologic solution at 37° C. The perfusion is then switched to the solution A described in Example 1 and perfused for 10 minutes at 37° C. temperature for another 10 minutes. After 10 minutes, the perfusion is disconnected and the spleen is submitted to $^{31}$P-NMR analysis as described in Example 2.

Spleen is then transferred to the storage container filled with solution A and maintained at 4° C. as shown in FIG. 1B. Care is taken that the splenic cannula is completely submerged.

Prior to the organ transfer the container is preoxygenated with filtered mixture of oxygen and carbon dioxide 95/5% from the gas tank source kept outside of container. The container and the solution are kept aseptic at any time.

The spleen is gently submerged in the solution A and stored for 24 hours. After 24 hours, spleen is removed and the biochemical and physiological functions are determined by using $^{31}$P-NMR as described before.

B. The spleen is treated in the same way as described in A.

Storage contained connected with the attached portable perfusion pump is prepared as in A and the spleen is connected via the portal cannula to the perfusion pump. Perfusion is maintained at steady rate of 1 ml per minute. The perfusion is done at 4° C. with the solution A.

C. The spleen is treated a in A but storage solution A contains 10% of emulsified perfluorocarbon.

D. The spleen is treated as in B but storage solution A contains 10% of emulsified perfluorocarbon.

E. The spleen is treated as in A by perfusing it first with solution A at 37° C. for 10 minutes, then the temperature is dropped to 4° C. and the spleen is transferred to storage container and stored at 4° C. in solution A for 24 hours.

Under these conditions, the spleen retains its functional and anatomical integrity as evidenced by the biochemical tests and by $^{31}$P-NMR for more than 10 days.

EXAMPLE 9

Preservation of Isolated Brain for Transplantation

This example illustrates the long-term preservation of brain for transplantation.

A. The left carotid artery is cannulated, and the brain is carefully removed from the rat's skull with care being taken that no injury to the brain occurs and that the cannula is at all time connected to the perfusion pump and the brain is perfused. The brain is first perfused 10 minutes with the physiologic solution at 37° C. The perfusion is then switched to the solution C described in Example 1 and perfused for 10 minutes at 37° C. temperature. After 10 minutes, the perfusion is switched back to perfusion with solution A. The brain is submitted to $^{31}$P-NMR analysis as described in Example 2.

Isolated brain with constant perfusion going on is then transferred extremely carefully to the storage container having a soft support on which the brain rests and which is filled with solution A and maintained at 4° C. as shown in FIG. 1B. Care is taken that the carotid artery cannula is completely submerged and immediately connected to perfusion pump. Prior to the organ transfer the container is preoxygenated with filtered mixture of oxygen and carbon dioxide 95/5% from the gas tank source kept outside of container. The container and the solution are kept aseptic at any time.

The brain are gently submerged in the solution A and stored for 24 hours. After 24 hours, brain is removed and the biochemical under constant perfusion and physiological functions are determined by using $^{31}$P-NMR.

B. The brain is treated in the same way as described in A.

Storage contained connected with the attached portable perfusion pump is prepared as in A and the brain is connected via the portal cannula to the perfusion pump. Perfusion is maintained at steady rate of 4 ml per minutes. The perfusion is done at 4° C. with the solution A containing medium 199 with essential amino acids.

C. The brain is treated as in A but storage solution A contains 10% of emulsified perfluorocarbon.

D. The brain is treated as in B but storage solution A contains 10% of emulsified perfluorocarbon.

E. The brain is treated as in A by perfusing it first with solution A at 37° C. for 10 minutes, then the temperature is dropped to 4° C. and then transferred to storage container and stored at 4° C. in solution A for 24 hours.

Under these conditions, the brain retain its functional and anatomical integrity as evidenced by the biochemical tests and by $^{31}$P-NMR for 24 hours.

EXAMPLE 10

Preservation of Isolated Cartilage, Cornea and Skin for Transplantation

Skin, cartilage or cornea are aseptically removed from the donor and dropped into the perfusion chamber with the perfusion chamber with warm (37° C.) circulating solution A. After 10 minutes, when the organs are thoroughly washed from all remnants of the blood and tissue debris, they are gently removed and dropped into container solution A at 4° C. oxygenated with mixture of oxygen and carbon dioxide, as described in Example 6 and stored until transplanted.

These organs stored in the solution A are fully functional after 2 months of storage.

What is claimed is:

1. An organ preservation solution suitable for long-term preservation of liver, kidney, spleen, heart-lung, pancreas, cartilage, skin and cornea for transplantation, consisting of pyruvate, inorganic salts providing ions to retain the cell action potential across the membrane and a protein selected from the group consisting of albumin and fetal calf serum.

2. The solution of claim 1 wherein the inorganic salts providing the ions are sodium chloride, potassium chloride, calcium chloride, sodium bicarbonate, sodium ethylenediaminetetraacetic acid, and magnesium salt.

3. The solution of claim 2 wherein the protein is fetal calf serum, synthetic or natural albumin, and the magnesium salt is magnesium chloride or magnesium sulfate.

4. The solution of claim 3 comprising 90–120 mM of sodium chloride, 4–4.5 mM of potassium chloride, 0.5–2.5 mM of calcium chloride, 22–28 mM of sodium bicarbonate, 0.0.5 mM of sodium ethylenediaminetetraacetic acid, 0.8–2 mM of magnesium sulfate or magnesium chloride, 6–15 mM of pyruvate and 0.01–1% of fetal calf serum or albumin.

5. The solution of claim 4 comprising 110 mM of sodium chloride, 4.3 mM of potassium chloride, 2 mM calcium chloride, 25 mM sodium bicarbonate, 0.5 mM of sodium ethylenediaminetetraacetic acid, 1.2 mM of magnesium sulfate, 10 mM of sodium pyruvate and 0.1% of albumin.

6. The solution of claim 5 further containing 5–20% of fluorocarbon.

7. An organ preservation solution suitable for long-term preservation of liver, kidney, spleen, heart-lung, pancreas, cartilage, skin or cornea for transplantation comprising pyruvate, ethanol, inorganic salts providing ions to retain the cell action potential across the membrane, and a protein selected from the group consisting of albumin and fetal calf serum.

8. The solution of claim 7 wherein the inorganic salts providing the ions are sodium chloride, potassium chloride, calcium chloride, sodium bicarbonate, sodium ethylenediaminetetraacetic acid, and magnesium salt.

9. The solution of claim 7 wherein the protein is fetal calf serum, synthetic or natural albumin and the magnesium salt is magnesium chloride or magnesium sulfate.

10. The solution of claim 7 wherein 90–120 mM of sodium chloride, 4–4.5 mM or potassium chloride, 0.5–2.5 mM of calcium chloride, 22–28 mM of sodium bicarbonate, 0.05 mM of sodium ethanol and ethylenediaminetetraacetic acid, 0.8–2 mM of magnesium sulfate or magnesium chloride, 6–15 mM of pyruvate 0.1–6% of ethanol and 0.01–1% of fetal calf serum or albumin.

11. The solution of claim 7 comprising 100 mM of sodium chloride, 4.3 mM of potassium chloride, b 2 mM calcium chloride, 25 mM sodium bicarbonate, 0.5 mM of sodium ethylenediaminetetraacetic acid, 1.2 mM of magnesium sulfate, 10 mM of sodium pyruvate, 0.5–4% of ethanol and 0.1% of albumin.

12. The solution of claim 10 further containing 5–20% of fluorocarbon.

13. A method for preservation of the liver, kidney, spleen, heart-lung, pancreas, cartilage, skin or cornea for transplantation by perfusion of the liver, kidney, spleen, heart-lung, pancreas, cartilage, skin or cornea with a preservation solution consisting of 90–120 mM of sodium chloride, 4–4.5 mM of potassium chloride, 0.15–2.5 mM of calcium chloride, 22–28 mM of sodium bicarbonate, 0.0.5 mM of sodium ethylenediaminetetraacetic acid, 0.8–2 mM of magnesium sulfate or magnesium chloride, 6–15 mM of pyruvate, and 0.01–1% of fetal calf serum or albumin.

14. The method of claim 13 wherein the preservation solution comprises 110 mM of sodium chloride, 4.3 of potassium chloride, 2 mM calcium chloride, 25 mM sodium bicarbonate, 0.5 mM of sodium ethylenediaminetetraacetic acid, 1.2 mM of magnesium sulfate, 10 mM of sodium pyruvate, and 0.1% of albumin.

15. The method of claim 14 wherein at least ten minutes of the perfusion is at temperature between 30–37° C.

16. A method for preservation of the liver, kidney, spleen, heart-lung, pancreas, cartilage skin or cornea for transplantation by perfusion of the liver, kidney, spleen, heart-lung, pancreas, cartilage, skin and cornea with a preservation solution comprising 90–120 mM of sodium chloride, 4–4.5 mM of potassium chloride, 0.5–2.5 mM of calcium chloride, b 22–28 mM of sodium bicarbonate, 0.0.5 mM of sodium ethylenediaminetetraacetic acid, 0.8–2mM of magnesium sulfate or magnesium chloride, 6–15 mM of pyruvate, 0.1–6% of ethanol, and 0.01–1% of fetal calf serum or albumin.

17. The method of claim 13 wherein the preservation solution comprises 100 mM of sodium chloride, 4.3 of potassium chloride, 2 mM calcium chloride, 25 mM sodium bicarbonate, 0.5 mM of sodium EDTA, 1.2 mM of magnesium sulfate, 10 mM of sodium pyruvate, 4% of ethanol, and 0.1% of albumin.

18. The method of claim 14 wherein the perfusion is at temperature between 4°–37° C.

19. A method for preservation of the liver, kidney, spleen, heart-lung, pancreas, cartilage skin or cornea for transplantation comprising a perfusion of the liver, kidney, spleen, heart-lung, pancreas, cartilage, skin or cornea with a first preservation solution consisting essentially of pyruvate and inorganic salts providing ions to retain the cell action potential across the cell membrane at 37° C. temperature, followed with a perfusion of the liver, kidney, spleen, heart-lung, pancreas, cartilage, skin and cornea with a second solution consisting essentially of pyruvate, ethanol and inorganic salts providing ions to retain the cell action potential across the cell membrane at temperature from 4°–37° C. and storing the liver, kidney, spleen, heart-lung, pancreas, cartilage, skin or cornea in the first solution at temperature between 2°–10° C.

20. The method of claim 19 wherein the preservation period solution further comprises essential amino acids.

* * * * *